United States Patent [19]

Magarian et al.

[11] Patent Number: 5,015,666

[45] Date of Patent: May 14, 1991

[54] TRIARYLCYCLOPROPANES AS ANTIESTROGENS AND ANTITUMOR AGENTS

[75] Inventors: Robert A. Magarian; Joseph T. Pento, both of Norman, Okla.; Billy W. Day, Newtonville, Mass.

[73] Assignee: Board of Reagents of the University of Oklahoma, Norman, Okla.

[21] Appl. No.: 410,938

[22] Filed: Sep. 22, 1989

Related U.S. Application Data

[63] Continuation-in-part of Ser. No. 98,945, Sep. 21, 1987, Pat. No. 4,879,315, which is a continuation-in-part of Ser. No. 363,429, Mar. 30, 1982, abandoned, which is a continuation-in-part of Ser. No. 166,255, Jul. 7, 1980, abandoned, which is a continuation-in-part of Ser. No. 128,040, Mar. 7, 1980, abandoned.

[51] Int. Cl.$^5$ ............................................. A61K 31/03
[52] U.S. Cl. .................................. 514/754; 424/422; 424/430; 424/433
[58] Field of Search ................ 514/754; 424/422, 430, 424/433

[56] References Cited

U.S. PATENT DOCUMENTS 4,879,315 11/1989 Magarian et al. .................. 514/754

OTHER PUBLICATIONS

Magarian et al, "Systems of Cyclopropyl Analogs of Stilbene and Stilbenediol as Possible Antiestrogens", J. Pharm. Sci., vol. 64, No. 10, Oct. 1975, pp. 1626–1631.

*Primary Examiner*—Nathan M. Nutter
*Attorney, Agent, or Firm*—Dunlap, Codding, Peterson & Lee

[57] ABSTRACT

Triarylcyclopropane derivatives in which one or more of the aryl groups includes a hydroxy as a substituted or unsubstituted or alkoxy or side chain substituent. The compounds are useful as antiestrogens and anti-tumor agents.

28 Claims, No Drawings

TRIARYLCYCLOPROPANES AS ANTIESTROGENS AND ANTITUMOR AGENTS

GOVERNMENTAL SUPPORT FOR INVENTION

This invention was made with Government support under a grant from the National Cancer Institute (CA40458). The Government has certain rights in this invention.

CROSS-REFERENCE TO RELATED APPLICATIONS

This application is a continuation-in-part of U.S. patent application Ser. No. 098,945, filed Sept. 21, 1987 and now U.S. Pat. No. 4,879,315, which is a continuation-in-part of U.S. patent application Ser. No. 363,429, filed Mar. 30, 1982, and now abandoned, which is a continuation-in-part of U.S. patent application Ser. No. 166,255, filed July 7, 1980, and now abandoned which is a continuation-in-part of U.S. patent application Ser. No. 128,040, filed Mar. 7, 1980 and now abandoned. These applications are incorporated herein by reference.

FIELD OF THE INVENTION

This invention relates to triarylcyclopropane compounds and their use in mammals for producing antiestrogenic activity in the mammal, and for inhibiting the development of an estrogen-dependent tumor in the mammal.

SUMMARY OF THE INVENTION

The present invention comprises a compound having the formula:

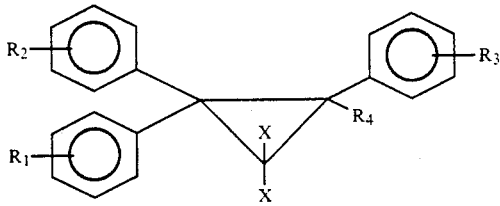

or any pharmaceutically acceptable salt thereof, in which $R_1$ is hydrogen, a hydroxyl group, an alkoxy group or a substituted or unsubstituted arylalkoxy group (with the proviso that $R_1$, $R_2$ and $R_3$ are not simultaneously arylalkoxy). Any substituent of the aryl group comprises an alkyl group. $R_2$ is hydrogen, a hydroxyl group (with the proviso that $R_1$ and $R_3$ are not simultaneously alkoxy when $R_2$ is hydroxyl), an alkoxy group or a substituted alkoxy group. The substituent of the alkoxy group comprises either a dialkylamino group, a heterocycle containing between about 5 and 6 members, at least one of which is nitrogen, or a substituted or unsubstituted aryl group, in which any substituent of the aryl group comprises an alkyl group. $R_3$ is hydrogen, a hydroxyl group, an alkoxy group or a substituted alkoxy group and in which the substituent of the alkoxy group comprises either a dialkylamino group, or a heterocycle containing between about 5 and 6 members, at least one of which is nitrogen, or a substituted or unsubstituted aryl group, in which any substituent of the aryl group comprises an alkyl group. $R_4$ is hydrogen, and X is a halogen or hydrogen. The compounds of the present invention may be combined with a pharmaceutically acceptable carrier to form pharmaceutical compositions.

The present invention further comprises a method of inducing antiestrogenic activity in a mammal in need of such therapy comprising administering to the mammal an antiestrogenically effective amount of one or more compounds having the above-described formula.

The present invention also comprises a method of inhibiting the development of an estrogen-dependent tumor in a mammal in need of such therapy comprising administering to the mammal an effective amount of one or more compounds having the above-described formula.

DETAILED DESCRIPTION OF THE PREFERRED EMBODIMENTS

The present invention comprises a compound having the formula:

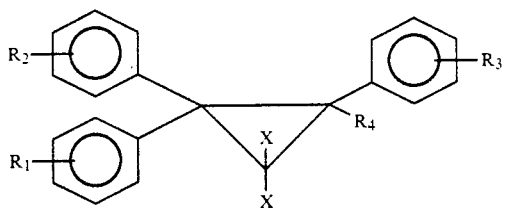

or any pharmaceutically acceptable salt thereof. $R_1$ represents a hydrogen, a hydroxyl group, an alkoxy group, preferably containing from 1 to about 3 carbon atoms, or a substituted or unsubstituted arylalkoxy group (with the proviso that $R_1$, $R_2$ and $R_3$ are not simultaneously arylalkoxy). The alkyl group attached to the oxygen atom in such an arylalkoxy group preferably contains from 1 to about 3 carbon atoms, and any substituent of the aryl group preferably comprises an alkyl group, preferably containing from 1 to about 3 carbon atoms.

In the compounds of the present invention $R_2$ is hydrogen, a hydroxyl group (with the proviso that $R_1$ and $R_3$ preferably are not simultaneously alkoxy when $R_2$ is a hydroxyl group), an alkoxy group, preferably containing from 1 to about 3 carbon atoms, or a substituted alkoxy group in which the alkyl group attached to the oxygen atom preferably contains from 1 to about 3 carbon atoms. The substituent of the alkoxy group preferably comprises either a dialkylamino group in which each alkyl substituent thereof preferably contains from 1 to about 3 carbon atoms, a heterocycle preferably containing between about 5 and 6 members, at least one of which is nitrogen, or a substituted or unsubstituted aryl group, in which any substituent of the aryl group preferably comprises an alkyl group preferably containing from 1 to about 3 carbon atoms.

$R_3$ in the compounds of the present invention is either hydrogen, a hydroxyl group, an alkoxy group, preferably containing from 1 to about 3 carbon atoms, or a substituted alkoxy group in which the alkyl group attached to the oxygen atom preferably contains from 1 to about 3 carbon atoms and in which the substituent of the alkoxy group preferably comprises either a dialkylamino group in which each alkyl substituent thereof preferably contains from 1 to about 3 carbon atoms, or a heterocycle preferably containing between about 5 and 6 members, at least one of which is nitrogen, or a substituted or unsubstituted aryl group, in which any substituent of the aryl group preferably comprises an alkyl group preferably containing from 1 to about 3 carbon atoms.

$R_4$ is hydrogen, and X is a halogen or hydrogen. In a preferred embodiment $R_4$ is a halogen, and more preferably, is chlorine. Compounds within the scope of the present invention include both the (R) and (S) optical isomers having the formula described above, and racemic mixtures of these optical isomers.

One particularly preferred compound of the present invention comprises (R/S)-(Z)-1,1-dichloro-2,3-diphenyl-2-(4-methoxyphenyl)cyclopropane including each of its (R) and (S) optical isomers:

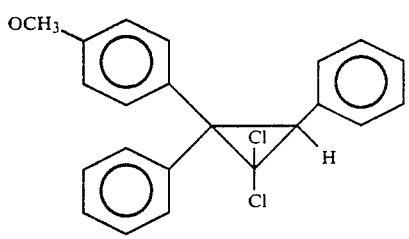

Another preferred compound is (Z)-1,1-dichloro-2,3-diphenyl-2-[4[2-(dimethylamino)-ethoxy]phenyl]cyclopropane, citrate salt:

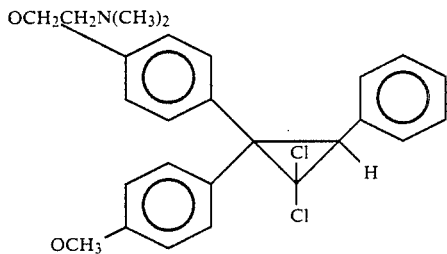

including each of its (R) and (S) optical isomers and racemic mixtures thereof.

Another preferred compound is (Z)-1,1-dichloro-2-[4-[2-(dimethylamino)-ethoxy]phenyl]-2-(4-methoxyphenyl)-3-phenylcyclopropane:

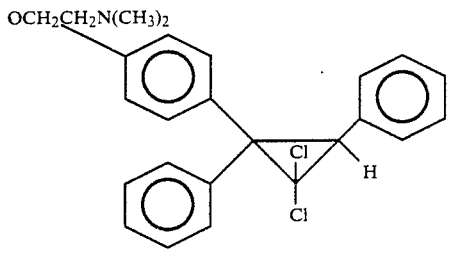

including each of its (R) and (S) optical isomers and racemic mixtures thereof.

Another preferred compound is (Z)-1,1-dichloro-2-(4-benzyloxyphenyl)-2-(4-methoxyphenyl)-3-phenylcyclopropane:

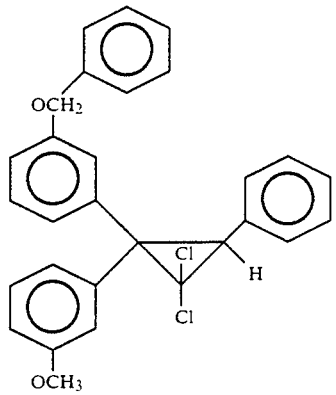

including each of its (R) and (S) optical isomers and racemic mixtures thereof.

Yet another preferred compound is (E) and (Z)-1,1-dichloro-2-(4-benzyloxyphenyl)-2,3-bis-(4-methoxyphenyl)cyclopropane:

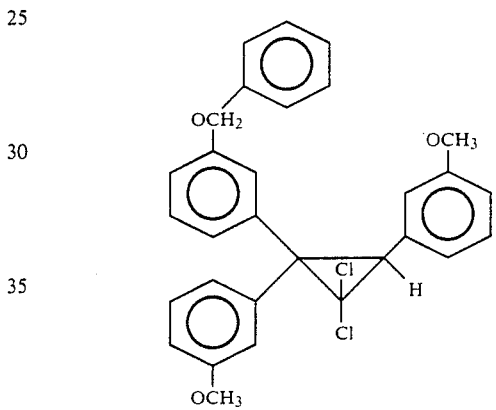

including each of its (R) and (S) optical isomers and racemic mixtures thereof.

Preferably, the compounds of the present invention are combined with a pharmaceutically acceptable carrier to form a pharmaceutical composition appropriate for therapeutic delivery to a mammal. The pharmaceutically acceptable carrier should not substantially interfere with the anti-estrogenic and anti-tumor activities of the compound, and may be a solid or liquid in which the compound is solubilized, suspended or dispersed in any manner. The compounds of the present invention may be administered orally in solid dosage forms, such as tablets, and powders, or in liquid dosage forms, such as elixirs, syrups and suspensions; they may also be administered parenterally, in sterile liquid dosage forms. Such parenteral administration may include intravenous, intramuscular, subcutaneous, intra-arterial, and direct tumor perfusion techniques.

If the compound is to be injected, the pharmaceutical carrier should preferably be isotonic, and have about a physiological pH. Suitable pharmaceutical carriers for parenteral administration may be any suitable oil, saline, aqueous dextrose or related sugar solutions, or glycols such as propylene glycol or polyethylene glycols. Solutions for parenteral administration contain preferably a water soluble salt of the active ingredient, suitable stabilizing agents, and if necessary, buffer substances. Additionally, parenteral solutions can contain preservatives. Other suitable pharmaceutical carriers are described in *Remington's Pharmaceutical Sciences*, Mack Publishing Co., and similar reference texts.

The present invention further comprises a method of inducing antiestrogenic activity in a mammal, such as a human, in need of such therapy comprising administering to the mammal an antiestrogenically effective amount of one or more compounds having the formula, preferably in the form described above. The dosage of the compounds of the present invention may vary due to the therapeutically desired result which is affected by the type of disease or condition in the mammal; the age, weight and health of the recipient; the severity of the condition or disease in the mammal; the kind of concurrent treatment, if any, being administered to the mammal; and the frequency of treatment. Generally, a therapeutically effective dosage is less than about 0.5 mg to about 2 mg per kilogram of body weight of the mammal over a 24 hour period. The method of administration of the compound of the present invention can be by any suitable method as previously described.

The present invention also comprises a method of inhibiting the development of an estrogen-dependent tumor in a mammal, such as a human, in need of such therapy comprising administering to the mammal a therapeutically effective amount of one or more compounds having the formula described above, preferably in the form of a pharmaceutical composition comprising at least one of the compounds combined with a pharmaceutically acceptable carrier. "Inhibiting the development of an estrogen-dependent tumor" means either slowing the growth of a tumor, diminishing the size of a tumor, or preventing the formation of a tumor from cells having the potential of developing into a tumor wherein the tumor requires the presence of an estrogenic substance for the growth, development and/or metastatic involvement of the tumor.

The compounds previously described may be administered to the mammal to inhibit the development of the estrogen-dependent tumor by an administration method of the type previously described. The dosage may vary according to the type of the disease; the size of the tumor or tumors, if present; and the quantity of tumors as well as other factors previously described. Generally, a daily dosage of less than about 0.5 mg to about 2 mg/kg of body weight of the mammal will suffice.

The following examples illustrate the practice of the present invention.

EXAMPLE 1

Synthetic Preparation of the Compounds of the Present Invention

Exemplary compounds of the present invention include compounds 4a–8 described in Table I.

TABLE I

Physical Characteristics of 1,1-Dichloro-2,2,3-triarylcyclopropanes.

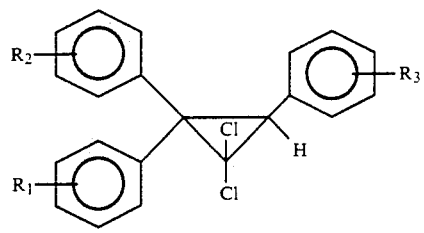

| Compound No. | $R_1$ | $R_2$ | $R_3$ | Formula[b] |
|---|---|---|---|---|
| 4a | H | H | H | $C_{21}H_{16}Cl_2$[d] |
| 4d* | $OCH_3$ | $OCH_2Ph$ | $OCH_3$ | $C_{30}H_{26}Cl_2O_3$[f] |
| 4e | $OCH_3$ | $OCH_3$ | $OCH_3$ | — |
| 5a | H | $OCH_3$ | H | $C_{22}H_{18}Cl_2O$[f] |
| 5b | $OCH_3$ | H | H | $C_{22}H_{18}Cl_2O$[f] |
| 5c | $OCH_3$ | $OCH_2Ph$ | H | $C_{29}H_{24}Cl_2O_2$[f] |
| 5d | $OCH_2Ph$ | $OCH_3$ | H | $C_{29}H_{24}Cl_2O_2$[f] |
| 6a | H | OH | H | $C_{21}H_{16}Cl_2O$ |
| 6b | $OCH_3$ | OH | H | $C_{22}H_{18}Cl_2O_2$ |
| 6c | OH | $OCH_3$ | H | $C_{22}H_{18}Cl_2O_2$ |
| 7a | H | $O(CH_2)_2NMe_2$ | H | $C_{31}H_{35}Cl_2NO_8$ |
| 7b | $OCH_3$ | $O(CH_2)_2NMe_2$ | H | $C_{26}H_{27}Cl_2NO_2$ |
| 8* | $OCH_3$ | OH | $OCH_3$ | $C_{23}H_{20}Cl_2O_3$[f] |

[b]All compounds gave combustion elemental analysis for C, H, and Cl that were within 0.4% of theoretical values, or formulas were confirmed by FAB-MS.
[c]Petroleum ether.
[d]See Dehmlow, E.V.; Schonefeld, J. Liebigs Ann. Chem. 1971, 744, 42.
[e]Et₂O/petroleum ether.
[f]Determined as a 1:1 mixture of (E)- and (Z)-isomers.
[g]Me₂CO/petroleum ether.
[h]SiO₂ chromatography.
*Mixture of (E)- and (Z)-isomers.

The general synthetic route to the compounds of the present invention is the addition of para-methoxy or para-benzyloxy substituted Grignard reagents to para-methoxy or para-benzyloxy protected or unsubstituted deoxybenzoins, followed by acid-catalyzed dehydration of the resulting carbinols to give a mixture of (E)- and (Z)-olefins as described in the Examples. These olefins reacted with dichlorocarbene to give fully protected compounds as described in greater detail in Examples 2–18.

The structures of all compounds were supported by their proton NMR spectra, which were performed on either a Varian EM-360A or an XL-300 spectrometer. The spectra are reported in parts per million in CDCl₃ with TMS, tetramethylsilane, as the internal standard. $^{13}$C-NMR were determined on a Varian XL-300 spectrometer at 75.5 MHz, referenced by the CDCl₃ signal. Gas chromatography/mass spectral analyses were performed in the EI mode on a Hewlett-Packard 5995 GC/MS system using a 30 m×0.25 mm DB-1 fused silicon capillary column (J and W scientific). Positive ion FAB-MS were determined on a VG analytical ZAB-E spectrometer at 0° C. in a 3-nitrobenzyl alcohol matrix ionized at 0.95 to 2 volts with the source operated at 8 kV using xenon as the discharge gas. High resolution spectra were calibrated with CsNaRbI. Infrared spectra were obtained from KBr pellets on a Beckman Acculab 1 spectrometer. Silica gel (J. T. Baker) of approximately 40 μm diameter was used for flash chromatography, which was performed at 5–10 psi. Petroleum ether was of bp 30°–60° C.

All organic starting materials and reagents were obtained from Aldrich Chemical Co. and were used without additional purification, unless otherwise indicated. Inorganic reagents were obtained from Fisher Scientific. Solvents were of the highest available grade and were obtained from Aldrich, Fisher, or J. T. Baker Chemical Co. Absolute ethanol was purchased from U.S. Industrial Chemicals Co. When necessary, solvents or reagents were dried by appropriate methods. Evaporations were carried out in vacuo on a rotary evaporator or under a stream of dry $N_2$. Melting points were taken on a Thomas-Hoover capillary melting point apparatus and are uncorrected. Reaction progress and product purity were monitored by analytical TLC on strips of Eastman Kodak plastic-backed $SiO_2$ 60 $F_{254}$ or $Al_2O_3$ $F_{254}$. Developed strips were viewed under light of 254- and 366-nm wavelengths. Elemental analyses were done by Midwest Microlab Ltd., Indianapolis, Ind. Analytical results were within ±0.4% of theoretical values. Acceptable elemental results are denoted by the formula, followed by the elements analyzed. Yields are based on pure samples, unless otherwise noted.

EXAMPLE 2

Preparation of Benzyl 4-bromophenyl ether

4-Bromophenol (17.3 g, 0.1 mol), 19.03 g (0.15 mol) benzyl chloride, and 27.64 g (0.2 mol) pulverized $K_2CO_3$ were suspended in 150 mL $Me_2CO$ and heated to reflux 2 h. The resulting suspension was concentrated on a rotary evaporator. The mixture was then diluted with 200 mL 5% NaOH and extracted with 100 mL $Et_2O$. The organic layer was washed with an additional 100 mL 5% NaOH, dried ($MgSO_4$), filtered, and concentrated to give a yellow oil, which was crystallized and recrystallized from boiling EtOH to yield 17 g (65%) of Benzyl 4-bromo phenyl ether as white needles, mp: 60°–61° C. NMR $\delta$ 7.35 and 6.82 (AA'BB', c, 4H, $C_6H_4$), 7.36 (s, 5H, $C_6H_5$), 5.0 (s, 2H, $OCH_2$).

EXAMPLE 3

Preparation of Benzyl 4-Benzyloxyphenyl Ketone

Benzyl 4-hydroxyphenyl ketone (5.1 g; 24 mmol), 3.8 g (3.5 mL, 30 mmol) of benzyl chloride, and 16.6 g (120 mmol) of pulverized and flame dried $K_2CO_3$ were slurried in 75 mL dry $Me_2CO$ under Ar. The mixture was heated to reflux 16 h, cooled to room temperature, diluted with $CH_2Cl_2$ (100 mL), and filtered. The resulting filter cake was washed with $C_6H_6$ (50 mL) and EtOAc (50 mL). The combined filtrates were concentrated and the resulting orange oil was dissolved in $C_6H_6$, washed with 10% $K_2CO_3$ (100 mL), 5% NaOH (2×50 mL), and $H_2O$ (100 mL). The organic layer was dried ($MgSO_4$), filtered, and concentrated to give 10 g of a light orange solid, which was purified on 60 g flash $SiO_2$ (1:1 petroleum ether-$CH_2Cl_2$) to give Benzyl 4-benzyloxphenyl ketone as a clear oil which was crystallized from $C_6H_6$-EtOH to yield 3.1 g of white needles (43%). mp: 134.5°–136° C. NMR $\delta$ 8.03 and 7.03 (AA'BB', c, 4H, ArH), 7.43 (s, 5H, ArH), 7.31 (s, 5H, ArH), 5.15 (s, 2H, $PhCH_2O$), 4.25 (s, 2H, $COCH_2$).

EXAMPLE 4

Preparation of 1,2-Diphenyl-1-(4-Methoxyphenyl)Ethene

To the Grignard reagent prepared from 4-bromoanisole (10 g, 53.5 mmol) and Mg turnings (1.32 g, 54.3 mg-atom) in 25 mL $Et_2O$ was added deoxybenzoin (9.81 g, 50 mmol) in 75 mL $Et_2O$ dropwise under reflux. After stirring at reflux 3 h, the mixture was carefully poured onto 1N $H_2SO_4$ and ice. The layers were allowed to separate and the aqueous layer was extracted with 25 mL $Et_2O$. The ether layers were combined, washed with $H_2O$ (2×80 mL), dried ($Na_2SO_4$), and concentrated to give a yellow oil which solidified at room temperature (14.2 g, 93.3% crude yield). Recrystallization from 95% EtOH gave 1,2-diphenyl-1-(4-methoxyphenyl)ethanol as a white powder mp: 111°–112° C. (lit. 112°–113° C.); NMR $\delta$ 7.2 (m, 14H, ArH), 3.75 (s, 3H, $OCH_3$), 3.63 (s, 2H, $CH_2$), 2.35 (brs, 1H, OH). The tertiary carbinol (14 g, 46 mmol) and p-TsOH.$H_2O$ (1 g, 5.31 mmol) were dissolved in 40 mL dry $C_6H_6$, heated to reflux, and stirred 2 h. The red mixture was cooled to room temperature and washed with 5% $NaHCO_3$ (2×75 mL). The combined aqueous layers were extracted with 25 mL $C_6H_6$. The organic layers were combined, washed with 100 mL $H_2O$, dried ($Na_2SO_4$), and concentrated to give a yellow oil. The (E)- and (Z)-olefin mixture was purified on 60 g flash $SiO_2$ (petroleum ether) and 1,2-Diphenyl-1-(4-methoxyphenyl)ethene was obtained as a clear oil (8 g, 61%); NMR $\delta$ 7.15 (m, 10H, ArH), 6.9 (s, 1H, C=CH), 6.8 (AA'BB', c, 4H, $MeOC_6H_4$), 3.71 (d, 3H, (E)- & (Z)-$OCH_3$).

EXAMPLE 5

Preparation of 1-(4-Benzyloxyphenyl)-1-(4-methoxyphenyl)-2-phenylethene

To the Grignard reagent prepared from 1.52 g (63 mg-atom) Mg turnings and 13.45 g (9 mL, 72 mmol) 4-bromoanisole (initiated with one $I_2$ crystal and one drop $EtBr_2$) in 25 mL THF was added 3 g (9.9 mmol) of Benzyl 4-benzyloxyphenyl ketone, prepared in Example 3. The reaction mixture was stirred at reflux for 48 h and then treated with 10 mL aqueous $NH_4Cl$. After cooling to room temperature, the slurry was filtered, the filter cake washed with 50 mL THF, and the filtrates concentrated to give an orange oil. The oil was chromatographed over 60 g flash $SiO_2$ (petroleum ether followed by $Me_2CO$). The $Me_2CO$ fractions were combined, concentrated, dissolved in 100 mL 1:1 95% EtOH-2N $H_2SO_4$, and refluxed with stirring for 8 h. The solvents were removed to give a brown gum, which was dissolved in 100 mL $Et_2O$, washed with saturated aqueous $NaHCO_3$ (100 mL), brine (100 mL), and $H_2O$ (100 mL). The organic layer was dried ($MgSO_4$), filtered, and concentrated to give a brown oil. The oil was purified on 60 g flash $SiO_2$ (9:1 petroleum ether-$CH_2Cl_2$) to give 3.1 g of 1-(4-Benzyloxyphenyl)-1-(4-methoxyphenyl)-2-phenylethene (80%) as a clear oil. NMR $\delta$7.41 (brs, 5H, O-benzyl $C_6H_5$), 7.3 to 6.75 (m, 9H, substituted rings' ArH and C=CH), 7.11 (s, 5H,=C—$C_6H_5$), 5.05 (s, 2H, $OCH_2Ph$), 3.79 (s, 3H, $OCH_3$).

EXAMPLE 6

Preparation of 1-(4-Benzyloxyphenyl)-1,2-bis(4-methoxyphenyl)ethene

Benzyl 4-bromophenyl ether (13.155 g; 50 mmol), prepared in Example 2, in 20 mL THF was added to Mg turnings (1.17 g; 48 mg-atom) in 20 mL THF. Grignard reagent formation was facilitated by addition of a few drops of $EtBr_2$, one crystal of $I_2$, and heat. This mixture was stirred and heated to reflux for 2 h. 11.54 g (45 mmol) desoxyanisoin was added under reflux as a slurry in 60 mL THF. The resulting mixture was stirred at reflux for 18 h, cooled to room temperature, poured onto 200 g 2N $H_2SO_4$ and ice (1:1), and stirred at room temperature until the ice melted. The resulting mixture was placed in a separatory funnel and extracted with 200 mL $Et_2O$. The organic layer was washed with aqueous $Na_2SO_5$ (100 mL), and brine (2×100 mL). The combined aqueous layers were extracted with $Et_2O$ (50 mL). The combined organic layers were dried ($MgSO_4$), filtered, and concentrated to give 19 g of a wine colored oil, which was dissolved in $Et_2O$ and refrigerated to precipitate any unreacted deoxyanisoin. After filtration and concentration of the solution, the resulting oil was purified on 60 g flash $SiO_2$ (7:3 petroleum ether-$CH_2Cl_2$) to yield 12.4 g (65%) of 1-(4-Benzyloxyphenyl)-2,2-bis(4-methoxyphenyl)ethene as a yellow oil. NMR δ7.41 (s, 5H, O-benzyl $C_6H_5$), 7.35 to 6.57 (m, 13H, ArH and C=CH), 5.07 (s, 2H, $PhCH_2O$), 3.78 (s, 1.5H, geminal ring $OCH_3$), 3.77 (s, 1.5H, central ring $OCH_3$), 3.72 (s, 3H, vicinal ring $OCH_3$).

EXAMPLE 7

Preparation of 1,1,2-Tris(4-methoxyphenyl)ethene

To the Grignard reagent prepared from 20 g 4-bromoanisole (107 mmol) and 2.43 g Mg turnings (107 mg-atom) in 20 mL $Et_2O$ was added 19.25 g dry ($P_2O_5$) desoxyanisoin (76 mmol) as a solid in four portions, each followed by a 50 mL wash of $Et_2O$. The mixture was stirred at reflux 17 h, cooled to room temperature, poured onto 200 g ice and 40 mL 1N $H_2SO_4$, and filtered into a separatory funnel. 100 mL $Et_2O$ was added and the organic layer was washed with 100 mL $H_2O$ and saturated $NaHCO_3$ (2×100 mL). The organic layer was dried ($MgSO_4$), filtered, and the $Et_2O$ was removed under reduced pressure to give crude 1,1,2-Tris(4-methoxyphenyl)ethanol as an orange oil which crystallized (25 mL EtOH with a trace of $NH_4OH$) as an orange solid, 18.6 g (67% crude yield), mp: 109°–127° C.; NMR δ7.47 to 6.63 (m, 12H, ArH), 3.73 (3 overlapping s, 9H, $OCH_3$), 3.48 (s, 2H, $CH_2$), 2.27 (s, 1H, OH). p-TsOH.$H_2O$ (2 g; 10.5 mmol) and 18.5 g of the crude carbinol (50.8 mmol) were dissolved in 50 mL $C_6H_6$, heated to reflux 2 h, cooled to room temperature, and poured onto 75 mL 5% $NaHCO_3$. The organic layer was washed with 75 mL 5% $NaHCO_3$. The combined aqueous layers were extracted with 25 mL $C_6H_6$. The combined organic layers were washed with 100 mL $H_2O$, dried ($Na_2SO_4$), filtered, and the solvent removed to give a dark oil. The oil was purified on 80 g flash $SiO_2$ (gradient elution with petroleum ether-$CH_2Cl_2$) yielding an amber oil which solidified at room temperature to yield 1,1,2-Tris(4-methoxyphenyl)ethene as white cubes (11.3 g, 64%), mp: 100°–101° C. (lit. 100°–101° C.). NMR δ7.29 to 6.55 (m, 13H, ArH and C=CH), 3.78 (s, 3H, geminal ring $OCH_3$), 3.75 (s, 3H, vicinal ring $OCH_3$), 3.69 (s, 3H, central ring $OCH_3$).

EXAMPLE 8

Preparation of 1,1-Dichloro-2,2,3-triphenylcyclopropane (Compound 4a)

Prepared in 64% yield from 3.2 g (12.5 mmol) of triphenylethylene (3.2 g; 12.5 mmol) and 0.25 g (1.1 mmol) benzyltriethylammonium chloride (TEBA) by dissolving in 50 g (419 mmol) $CHCl_3$, stirring rapidly at room temperature, and treating with 27 mL of chilled 50% aqueous NaOH dropwise according to the method of Dehmlow, E. V., et al., S.S. Phase Transfer Catalysis, *Verlag Chemie*: Deerfield Beach 1980. After stirring 75 h, the resulting mixture was poured onto 150 mL $H_2O$ and extracted with $CH_2Cl_2$ (2×100 mL). The combined organic layers were washed with 100 mL $H_2O$, dried ($Na_2SO_4$), filtered and concentrated. The resulting brown oil was dissolved in boiling petroleum ether, quickly filtered, and allowed to stand at room temperature, yielding 2.7 g (64%) of Compound 4a as a white powder, mp: 106°–107° C. (petroleum ether) (lit. 105°–107° C.); NMR δ7.23 (m, 15H, ArH), 3.57 (s, 1H, cyclopropyl H); IR ($CM^{-1}$) 3020, 3000, 1600, 1490, 1435, 860, 775 765, 750, 695; MS (m/z, % base) 342 (M+4), 3.2; 340 (M+2), 6.3; 338 (M+), 10.23; 303 (—Cl), 100; 267 (—Cl, —HCl), 80.7.

EXAMPLE 9

Preparation of (R/S) (E)-and (Z)-1,1-Dichloro-2-(4-benzyloxyphenyl)-2,3-bis-(4-methoxyphenyl)cyclopropane (Compound 4d)

1-(4-Benzyloxyphenl)-1,2-bis(4-methoxyphenyl)ethene (20 g; 47.4 mmol); prepared in Example 6, and 1 g TEBA (4.39 mmol) in 100 mL $CHCl_3$ were treated with 80 mL chilled 50% NaOH with rapid stirring for 30 h. This reaction was monitored by NMR (appearance of cyclopropyl H signal) since no suitable TLC solvent system was found. The dark emulsion was poured into a separatory funnel containing 100 mL $H_2O$ and 100 mL $CH_2Cl_2$. The aqueous layer was extracted with $CH_2Cl_2$ (2×50 mL). The combined organic layers were washed with $H_2O$ (3×100 mL), dried ($K_2CO_3$), filtered, and concentrated to yield a dark oil, which was dissolved in $C_6H_6$ and chromatographed on 200 g $Al_2O_3$ (Act. I, 1:1 $C_6H_6$-petroleum ether) under 5 psi. Fractions 2–6 (100 mL ea.) were concentrated to give an orange oil, which was dissolved in 200 mL petroleum ether containing ca. 10 mL $Et_2O$. After standing at room temperature 4 days, Compound 4d precipitated as a white powder. Four crops yielded 6.2 g (26%), mp: 127°–128° C. NMR (300 MHz) δ7.39 and 6.82 (AA'BB', c, 4H, J=8.5 Hz, ArH), 7.36 to 7.25 (m, 5H, $C_6H_5$), 7.19 and 6.80 (AA'BB', c, 4H, J=8.5 Hz, ArH), 6.91 and 6.74 (AA'BB', c, 4H, J=8.5 Hz, ArH), 4.92 (s, 2H, $OCH_2Ph$), 3.70 (s, 3H, $OCH_3$), 3.69 (s, 3H, $OCH_3$), 3.47 (s, 1H, cyclopropyl H). Anal. ($C_{30}H_{26}Cl_2O_3$) C, H, Cl. This compound readily decomposes in solution with evolution of HCl gas on contact with scratched, sintered, or ground glass.

EXAMPLE 10

Preparation of 1,1-Dichloro-2,2,3-tris(4-methoxyphenyl)cyclopropane (Compound 4(e))

1,1,2-Tris(4-methoxyphenyl)ethene (10 g; 29 mmol), prepared in Example 7, and 0.5 g of TEBA (2.2 mmol) were dissolved in 68 mL $CHCl_3$ and treated dropwise with 53 mL of chilled 50% NaOH. The mixture was stirred at room temperature 48 h. 100 mL $CH_2Cl_2$ was added and the aqueous layer was removed. The aqueous layer was taken to pH 7 with 1N HCl and extracted with 50 mL $CH_2Cl_2$. The combined organic layers were washed with 100 mL $H_2O$, dried ($MgSO_4$), filtered, and concentrated to give crude Compound 4e as a black oil (11.5 g, 92% crude yield). NMR δ7.47 to 6.62 (m, 12H, ArH), 3.8 (s, 3H, geminal ring $OCH_3$), 3.73 (s, 3H, vicinal ring $OCH_3$), 3.69 (s, 3H, central ring $OCH_3$), 3.5 (s, 1H, cyclopropyl H).

EXAMPLE 11

Preparation of (R/S) (Z)-1,1-Dichloro-2,3-diphenyl-2-(4-methoxy-phenyl)-cyclopropane (5a), and (E)-isomer (Compound 5b)

The mixture of (E)- and (Z)-olefins 1,2-Diphenyl-1-(4-methoxyphenyl)ethene (5 g, 17.5 mmol), prepared in Example 4, and TEBA (0.25 g, 1.1 mmol) were dissolved in CHCl$_3$ (50 g, 419 mmol). Chilled 50% NaOH (26.7 mL) was added dropwise. The two phases were rapidly stirred at room temperature for 96 h. The resulting orange emulsion was poured onto 150 mL H$_2$O and extracted with CH$_2$Cl$_2$ (2×100 mL). The organic layers were combined, washed with 100 mL H$_2$O, dried (Na$_2$SO$_4$), and concentrated to give a dark oil. The mixture of cyclopropanes was isolated by flash chromatography (4:1 petroleum ether-CH$_2$Cl$_2$) as a white powder. Recrystallization from petroleum ether or pentane gave a mixture of 5a and 5b as a white amorphous solid (2.53 g, 38%): mp: 118°–123° C.; NMR δ7.15 (m, 14H, ArH), 3.76 (s, 3H, OCH$_3$), 3.52 (s, 1H, cyclopropyl H). IR (CM$^{-1}$) 3030, 3015, 3000, 2980, 2965, 2920, 1605, 1510, 1450, 1440, 1250, 1175, 1025, 870, 830, 770, 700; MS (m/z, % base) 334 (—Cl), 7.09; 297 (—Cl, —HCl), 100. Anal. (C$_{22}$H$_{18}$Cl$_2$O) C, H, Cl. The (Z)-isomer, Compound 5a, was isolated by fractional crystallization (petroleum ether/Me$_2$CO), 1.8 g (27%), mp: 132°–133.5° C.; NMR δ7.33 (s, 10H, ArH), 6.72 and 7.52 (AA'BB', c, 4H, central ring), 3.71 (s, 3H, OCH$_3$), 3.52 (s, 1H, cyclopropyl H). The (E)-isomer, Compound 5b, was obtained as clear crystals by thin layer chromatography (SiO$_2$, petroleum ether) as the more mobile compound, 0.7 g (11%), mp: 114.5°–116.5° C.; NMR δ7.33 (s, 10H, ArH), 6.92 and 7.33 (AA'BB', c, 4H, geminal ring), 3.79 (s, 3H, OCH$_3$), 3.52 (s, 1H, cyclopropyl H).

EXAMPLE 12

Preparation of (R/S) (Z)-1,1-Dichloro-2-(4-benyloxyphenyl)-2-(4-methoxy-phenyl)-3-phenylcyclopropane (5c) and (E)-isomer (Compound 5d)

1-(4-Benzyloxyphenyl)-1-(4-methoxyphenyl)-2-phenylethene (6 g; 15.3 mmol), prepared in Example 5, was dissolved in 100 mL CHCl$_3$ along with 0.5 g TEBA. The resulting solution was treated with 30 mL chilled 50% NaOH and rapidly stirred at room temperature 96 h. The resulting dark mixture was poured onto 200 mL CHCl$_3$ in a separatory funnel and the aqueous layer was carefully adjusted to pH 7 with 2N HCl. An additional 100 mL H$_2$O was used to wash the organic layer. The combined aqueous layers were extracted with 50 mL CHCl$_3$. The combined organic layers were dried (MgSO$_4$), filtered, and concentrated to give an orange oil. The oil was treated with Et$_2$O/petroleum ether to give a 1:1 mixture of (E) and (Z) isomers 4c: mp 129°–134° C.; Anal. C$_{29}$H$_{24}$Cl$_2$O$_2$ (C, H, Cl). The (Z)-isomer, Compound 5c, precipitated rapidly at room temperature from 75 mL boiling butanone as a white powder (two crops, 2.3 g, 32%); mp: 169°–171° C. NMR δ7.42 to 7.17 (m, 12H, ArH), 7.01 (m, 2H, ArH), 6.84 (d, 4H, J=8.7 Hz, ortho signals), 4.98 (s, 2H, OCH$_2$), 3.75 (s, 3H, OCH$_3$), 3.5 (s, 1H, cyclopropyl H). Recrystallization from boiling EtOAc raised the melting point to 173.5°–175° C. The (E)-isomer, Compound 5d, could be obtained by concentration of the mother liquor and purification over 60 g flash SiO$_2$ (4:1 petroleum ether-CH$_2$Cl$_2$), followed by recrystallization from boiling EtOH containing a trace of Et$_2$O (0.8 g, 11%); mp: 133°–134° C. NMR δ 7.43 to 6.95 (m, 9H, ArH), 7.36 (s, 5H, O-benzyl C$_6$H$_5$), 7.1 (d, 2H, J=8.7 Hz, meta signals), 6.78 (d, 2H, J=8.7 Hz, meta signals), 5.03 (s, 2H, OCH$_2$), 3.73 (s, 3H, OCH$_3$), 3.5 (s, 1H, cyclopropyl H).

EXAMPLE 13

Preparation of (R/S) (Z)-1,1-Dichloro-2,3-diphenyl-2-(4-hydroxyphenyl)cyclopropane (Compound 6a)

To cooled n-BuSH (0.63 g, 7 mmol) in 6 mL CH$_2$Cl$_2$ was added AlCl$_3$ (0.75 g, 6 mmol) under Ar. The methoxy Compound 5a (0.5 g, 1.35 mmol), prepared in Example 11, in 15 mL CH$_2$Cl$_2$ was added dropwise at 0° C. After stirring 2 h at room temperature the reaction was quenched with 20 mL H$_2$O. The yellow mixture was extracted with Et$_2$O (2×40 mL). The combined organic layers were washed with 30 mL 0.1N H$_2$SO$_4$, dried (Na$_2$SO$_4$), and concentrated to give 475 mg of an amber oil. Flash chromatography on 20 g SiO$_2$ (1:1 CH$_2$Cl$_2$-petroleum ether) yielded 400 mg of an off-white glass. Crystallization from EtOH yielded 400 mg of Compound 6a as white needles (84%): mp: 135.5°–136° C.; NMR δ7.38 and 6.58 (AA'BB', c, 4H, central ring), 7.02 (m, 10H, ArH), 4.75 (brs, 1H, OH), 3.53 (s, 1H, cyclopropyl H). IR (CM$^{-1}$) 3305, 3030, 3010, 1600, 1505, 1490, 1450, 1440, 1210, 1155, 865, 820, 765, 720. MS (m/z, % base) 320 (—Cl), 6.96; 319 (—HCl, 6.03); 318 (—H, —HCl, 27.05); 283 (-2HCl, 100). Anal. (C$_{21}$H$_{16}$Cl$_2$O) C, H, Cl.

EXAMPLE 14

Preparation of (R/S) (E)-1,1-Dichloro-2-(4-hydroxyphenyl)-2-(4-methoxyphenyl)-3-phenylcyclopropane (Compound 6b)

Benzyl ether 5c (1 g; 2.1 mmol), prepared in Example 12, was dissolved in 50 mL dry THF and hydrogenolyzed in the presence of 50 mg 5% Pd/C at one atmosphere and room temperature for 8 h. The resulting clear solution was filtered, concentrated to give a red oil, and purified on 20 g flash SiO$_2$ (1:1 petroleum ether-CH$_2$Cl$_2$) to yield 0.8 g (99%) of Compound 6b as an orange semi-solid. NMR δ7.31 to 6.94 (m, 7H, ArH), 7.3 (d, 2H, J=8.7 Hz, meta signals), 6.83 (d, 2H, J=8.7 Hz, ortho signals), 6.65 (d, 2H, J=8.7 Hz, ortho signals), 5.75 (brs, 1H, OH), 3.7 (s, 3H, OCH$_3$), 3.5 (s, 1H, cyclopropyl H). An analytical sample was obtained by drying over P$_2$O$_5$ at 60° C. 6 h. Anal. C$_{22}$H$_{18}$Cl$_2$O$_2$ (C, H, Cl).

EXAMPLE 15

Preparation of (R/S) (Z)-1,1-Dichloro-2-(4-hydroxyphenyl)-2-(4-methoxyphenyl)-3-phenylcyclopropane (Compound 6c)

Benzyloxy ether 5d (2 g; 4.2 mmol), prepared in Example 12, was hydrogenolyzed in 60 mL dry THF with H$_2$ in the presence of 110 mg 5% Pd/C for 4 h. The resulting clear solution was filtered, concentrated, and purified on 45 g flash SiO$_2$ (1:1 petroleum ether-CH$_2$Cl$_2$) to yield 1.6 g (99%) of Compound 5c as a red oil. A small amount crystallized after dissolving in toluene and treating the solution with hexane, mp: 133°–135° C. NMR δ7.55 to 6.83 (m, 8H, ArH), 7.3 (s, 5H, C$_6$H$_5$), 5.53 (brs, 1H, OH), 3.69 (s, 3H, OCH$_3$), 3.5 (s, 1H, cyclopropyl H). Anal. C$_{22}$H$_{18}$Cl$_2$O$_2$ (C, H, Cl).

EXAMPLE 16

Preparation of (R/S) (Z)-1,1-Dichloro-2,3-diphenyl-2-[4-[2-(dimethylamino)ethoxy]-phenyl]cyclopropane, dihydrogen citrate salt (Compound 7a)

Phenol 6a (1.25 g; 3.52 mmol), prepared in Example 13, 0.58 g of N,N-dimethylaminoethyl chloride hydrochloride (4 mmol), and 1.38 g pulverized and flame-dried $K_2CO_3$ (10 mmol) were slurried in 20 mL dry $Me_2CO$ under Ar and heated to reflux overnight. The resulting brown slurry was cooled to room temperature, filtered, and concentrated to give a brown oil. This was dissolved in 30 mL $Et_2O$ and washed with 1N NaOH ($2 \times 40$ mL). The combined aqueous layers were extracted with 25 mL $Et_2O$. The combined organic layers were washed with 40 mL brine, $H_2O$ ($2 \times 20$ mL), dried ($MgSO_4$), filtered, and concentrated to give a brown gum. The crude material was dissolved in $MeOH$-$Et_2O$, 2 mL 30% HCl was added, and the mixture was stirred at room temperature 0.5 h. The solvents were removed to give a brown glass. The glass was treated with 30% NaOH up to pH 11 and 50 mL $Et_2O$ was added. The organic layer was washed with 10% NaOH ($2 \times 50$ mL), 50 mL brine, and 50 mL $H_2O$. The organic layer was dried ($K_2CO_3$), filtered, and concentrated to give a brown oil. This was loaded on a 20 mL basis $Al_2O_3$ (activity I) column and eluted with $CH_2Cl_2$. A yellow oil was collected which had spectral features of the desired product: NMR $\delta 7.73$ to 7.02 (m, 12H, ArH), 6.85 (d, J=9 Hz, central ring 2H ortho to O), 4.03 (t, J=5.5 Hz, 2H, $OCH_2$), 3.52 (s, 1H, cyclopropyl H), 2.69 (t, J=5.5 Hz, 2H, $CH_2N$), 2.3 (s, 6H, $NMe_2$). The oil was dissolved in hot EtOH and treated with excess anhydrous citric acid in hot EtOH. Treatment of the cooled solution with $Et_2O$ yielded 0.11 g (5%) of Compound 7a in two crops as a white powder mp: 140°–142° C. Anal. ($C_{25}H_{25}Cl_2NO \cdot C_6H_8O_7$) C, H, Cl, N.

EXAMPLE 17

Preparation of (R/S) (Z)-1,1-Dichloro-2-[4-[2-(dimethylamino)ethoxy]-phenyl]-2-(4-methoxyphenyl)-3-phenylcyclopropane (Compound 7b)

Phenol 6b (1.45 g; 3.78 mmol), prepared in Example 14, 1.63 g (11.3 mmol) of N,N-dimethylaminoethyl chloride hydrochloride, and 5.2 g (38 mmol) of dry, pulverized $K_2CO_3$ in 60 mL of dry $Me_2CO$ were stirred and heated to reflux under Ar 24 h. The resulting slurry was cooled to room temperature, filtered, and concentrated. The resulting oil was dissolved in 60 mL EtOAc and washed with 10% NaOH ($2 \times 50$ mL). The combined aqueous layers were extracted with 25 mL EtOAc. The combined organic layers were washed with $H_2O$ ($2 \times 50$ mL), dried ($K_2CO_3$), filtered, and concentrated to give a dark oil, which was initially purified on 20 g flash $SiO_2$ (9:1 $C_6H_6$-$Et_3N$), followed by two further purifications on flash $SiO_2$ (20 g each, $Me_2CO$) to give 225 mg (13%) of Compound 7b as a yellow gum. NMR $\delta 7.57$ to 6.78 (m, 13H, ArH), 4.08 (t, 2H, J=5 Hz, $OCH_2$), 3.8 (s, 3H, $OCH_3$), 3.53 (s, 1H, cyclopropyl H), 2.75 (t, 2H, J=5 Hz, $CH_2N$), 2.37 (s, 6H, $N(CH_3)_2$). FAB-MS (m/z, % base): 458 (M+H+2), 25.8; 456 (M+H), 50.3; 421 (M+H-Cl), 100. High resolution FAB-MS: $C_{26}H_{27}Cl_2NO_2$ calculated for 455.1419, found 455.1496.

EXAMPLE 18

Preparation of (R/S) (E)- and (Z)-1,1-Dichloro-2-(4-hydroxyphenyl)-2,3-bis-(4-methoxyphenyl)cyclopropane (Compound 8)

Benzyl ether 4d (0.5 g; 0.99 mmol), prepared in Example 9, in 20 mL THF was treated with $H_2$ in the presence of 150 mg 5% Pd/C at one atmosphere and ambient temperature for 4.5 h. The mixture was filtered, concentrated, and crystallized from $Et_2O$/petroleum ether to give white solid that tenaciously held $Et_2O$, even after drying ($P_2O_5$, 0.1 mm Hg, 40° C., 18 h) in an Abderhalden apparatus, mp: 105°–106° C. (dec., with prior softening). Elemental analysis and NMR showed 1.8 molecules of $Et_2O$ per molecule of 8. Several recrystallizations from $C_6H_6$/hexane yielded 3.9 g (95%) of the product as a white powder, mp: 96°–97° C. (dec.). NMR $\delta 7.45$ (d, 2H, meta signals), 7.3 to 6.64 (m, 11H, ArH+OH), 3.81 (s, 3H, $OCH_3$), 3.79 (s, 3H, $OCH_3$), 3.49 (s, 1H, cyclopropyl H). This powder would not give a satisfactory combustion elemental analysis, and was subjected to FAB-MS (m/z, % base): 419 (M+H+4), 1.1; 417 (M+H+2), 2.1; 415 (M+H), 3.1; 381 (M+2-Cl), 33.6; 379 (M-Cl), 100; 343 (—HCl, —Cl), 34.

EXAMPLE 19

Biological Testing

The biological evaluation of the test compounds consisted of the in vitro rat cytosolic estradiol receptor binding assay, the in vivo immature mouse uterotrophic (estrogenic) assay, and the in vivo immature mouse and rat antiuterotrophic (antiestrogenic) assay and in the in vitro suppression of the proliferation of the MCF-7 human breast cancer cell line (Table II). All assays contained estradiol, TAM, MER 25, and 1-1-dichloro-2-3-cis-diphenylcyclopropane (Analog II) as standards.

Biological Assays. Tamoxifen was obtained from Stuart Pharmaceutical, Division of ICI Americas, Inc., Wilmington, Del. MER 25 was obtained from Merrell Dow Research Institute, Division of Merrell Dow Pharmaceuticals, Inc., Cincinnati, Ohio. Absolute ethanol was obtained from U.S. Industrial Chemicals Co. Hormones and biochemicals were purchased from Sigma Chemical Co. Animals and Housing. Viral-free immature female Swiss-Webster mice were obtained at 17–19 days of age from Sasco (Omaha, Nebr.) weighing 8–10 g, and were used in the uterotrophic and antiuterotrophic assays. Immature female Sprague-Dawley rats, obtained also at 17–19 days of age from Sasco, weighing 28–33 g, were used in the estradiol receptor binding assay. Animals were housed in wire topped polycarbonate cages with six animals per cage. Environment was controlled at 25° C. with a 12-hour light/dark cycle. The animals received a diet of Wayne Lab Blox rodent chow and tab water ad libitum.

EXAMPLE 20

Receptor Binding Assay

The receptor binding activies of the test compounds for the estrogenic receptors were determined by displacement of [$^3$H]-estradiol from rat uterine cytosol in vitro. Female Sprague-Dawley rats (17–19 days old) were treated with 0.53 µg of estradiol in 0.1 mL sesame oil for three consecutive days (total dose 1.6 µg). On the fourth day the rats were anesthetized with $Et_2O$ and sacrificed by cervical dislocation. A modification of Korenman's receptor binding assay method (Korenman, S. G., *Steroids* 13: 163 (1969)) was used. Uteri were removed, cleaned of adhering connective tissue and fat, weighed (avg. wt.=83 mg/animal), and homogenized (Polytron PT-10 stainless steel homogenizer, rheostat setting 7, five ten-second bursts with a ten-second pause between bursts) at 0°–4° C. in five volumes (w/v) of TEDM buffer (10 mM Tris-HCl, 1.5 mM disodium ethylenediamine tetraacetic acid, 1.0 mM dithiothreitol, 10.0 mM sodium molybdate, pH adjusted to 7.4 with 5M NaOH). The resulting homogenate was centrifuged at 2000 g for 15 min (4° C.). The supernatant was then centrifuged at 104,000 g for 1 h (4° C.). The supernatant from the high speed centrifugation (cytosol) was carefully decanted and used immediately. The protein content of the cytosol was determined and adjusted to 4–5 mg protein/mL. The test compounds were dissolved in EtOH or DMSO and diluted with TEDM so that the final EtOH concentration was less than 2% or the final DMSO concentration was less than 10%. Neither of these concentrations of the organic solvents affected the binding of the tritiated estradiol to the cytosolic receptor or the amount of non-specific binding seen as determined by parallel incubations. Duplicate incubations were conducted at 4° C. for 24 h in a total volume of 0.5 mL containing: 200 μL cytosol; 100 μL (0.218 μCi) of 2,4,6, 7(n)-[$^3$H]-17β-estradiol (93.35 mCi/mmole); 100 μL of the test compounds at concentrations ranging from $10^{-4}$ to $10^{-6}$M, or unlabelled estradiol at concentrations ranging from $10^{-6}$ to $10^{-8}$M; and sufficient TEDM to obtain a final volume of 0.5 mL. Single parallel incubations at each concentration of test compound and estradiol contained 100 μL of $2 \times 10^{-5}$M DES in the final TEDM addition to distinguish between specific receptor binding and non-specific protein binding of the compounds.

After incubation, 0.5 mL of a dextran-coated charcoal (DCC) solution (0.5% activated charcoal and 0.05% Dextran T-70, w/v, in TEDM buffer) was added and the tubes were gently vortexed at 4° C. 15 min. The tubes were centrifuged at 2000 g 15 min (4° C.) to remove the unbound [$^3$H]-estradiol. A 0.5 mL aliquot of the supernatant was added to 10 mL Beckmann Ready-Solv VI scintillation cocktail in subdued light and the tritium content of each vial was determined by liquid scintillation spectrometry. The radioactivity was plotted as a function of the log concentration of competing ligand and subjected to linear regression analysis. Relative binding affinity of each compound was determined by the method of Bliss, C.I., *The Statistics of Bioassay*, Academic Press (New York 1952). The observed receptor binding activities are set out in Table II.

TABLE II

Estrogen Receptor Binding Affinities[a] and Antiestrogenic Activities[b] of 1,1-Dichloro-2,2,3-triarylcyclopropanes

| No. | RBA[c], % | dose (μg) | Antiestrogenic % Reduction[d] |
|---|---|---|---|
| 4a | 0.13 | 30 | 11 |
|  |  | 150 | 3 |
|  |  | 750 | 13 |
| 4d[e] | 0.08 | 10 | 2 |
|  |  | 30 | 15 |
|  |  | 150 | 49 |
|  |  | 750 | 2 |
| 5a | 0.25 | 30 | 22 |
|  |  | 150 | 48 |
|  |  | 750 | 33 |
| 5c | 0.09 | 30 | 37 |

TABLE II-continued

Estrogen Receptor Binding Affinities[a] and Antiestrogenic Activities[b] of 1,1-Dichloro-2,2,3-triarylcyclopropanes

| No. | RBA[c], % | dose (μg) | Antiestrogenic % Reduction[d] |
|---|---|---|---|
|  |  | 150 | 47 |
|  |  | 750 | 22 |
| 6a | 0.69 | 30 | 23 |
|  |  | 150 | 12 |
|  |  | 750 | 25 |
| 6b | 1.70 | 30 | 15 |
|  |  | 150 | −7 |
|  |  | 750 | 40 |
| 6c | 2.40 | 30 | 28 |
|  |  | 150 | 18 |
|  |  | 750 | 22 |
| 7a[f] | 0.87 | 4 | −6 |
|  |  | 10 | 10 |
|  |  | 30 | 37 |
|  |  | 150 | 30 |
|  |  | 750 | 18 |
| 7b | 0.73 | 4 | −10 |
|  |  | 10 | 6 |
|  |  | 30 | 33 |
|  |  | 150 | 42 |
|  |  | 750 | 53 |
| 8[e] | 3.62 | 30 | 19 |
|  |  | 150 | 10 |
|  |  | 750 | 26 |
| Tamoxifen | 0.87 | 30 | 4 |
|  |  | 150 | 0 |
|  |  | 750 | −13 |
| MER 25 | 0.0016 | 30 | 1 |
|  |  | 150 | 30 |
|  |  | 750 | 82 |
| Analog II | 0.0086 | 200 | 24 |
|  |  | 400 | 36 |
|  |  | 800 | 49 |
| Estradiol | 100 | — | — |

[a]Determined by competitive radiometric binding assay with rat uterine cytosol as a source receptor. [$^3$H]estradiol as tracer, and dextran-coated charcoal as absorbant for free ligand.
[b]Determined as the decrease in the estradiol-stimulated (0.03 μg total dose) uterine weight of immature (17–19 day old) female mice.
[c]Binding affinities are expressed relative to that of estradiol = 100% (RBA = relative binding affinity) and are the average of duplicate determinations minus non-specific binding.
[d]Calculated by: 100 − {(mean uterine weight of test compound treated animals − mean uterine weight of control animals)/(mean uterine weight of estradiol-stimulated animals − mean uterine weight of controls)} × 100.
[e]Determined as a 1:1 mixture of isomers.
[f]Dihydrogen citrate salt.

EXAMPLE 21

Uterotrophic Assay

Estrogenic activity of the compounds was determined using a modification of the method of Rubin, B. L., et al., *Endocrinology* 49: 429 (1951) (see Pento, J. T., et al.; 1 *J. Endocrinol.* 61: 1216 (1978)) using immature (17–19 days old) female Swiss-Webster mice. The test compounds were dissolved separately in a minimum amount of isopropyl myristate (IPM), and diluted serially with sesame oil to the proper concentrations (final concentration of IPM<5%). Solutions were shaken at 25° C. for several hours to ensure complete dissolution. The mice were randomly separated into groups of six animals, weighed, and the compounds were administered by s.c. injection of 0.1 mL of the oil solutions into the nape of the neck for 3 consecutive days. The solutions were periodically checked by TLC to insure homogeneity. A control group received 0.1 mL sesame oil alone.

The animals were anesthetized with Et$_2$O and sacrificed by cervical dislocation 24 h after the last injection. Body weights were determined and the uteri were removed, cleaned of adhering connective tissue and fat, blotted to remove tissue fluid, and weighed to the nearest 0.1 mg. The new compounds showed no significant uterotrophic activity at doses of 10, 50, and 250 µg (6a-b, 7a-b, 8, 10), or at doses of 30, 150, and 750 µg (4a, 4d, 5a, 5c, 6b, 9a-b). Tamoxifen elicited a significant estrogenic response at a total dose of 1 µg, while MER 25 was slightly estrogenic only at the high total dose of 750 µg.

EXAMPLE 22

Antiuterotrophic Assay

Antiestrogenic activity of the compounds was determined by inhibition of the estradiol-induced uterotrophic activity in immature female Swiss-Webster mice. Animals were distributed into groups of six animals. A modification of the uterotrophic assay described in Example 21 was used (Dorfman, R. I., et al., *Endocrinology* 68: 17 (1960)). Estradiol was dissolved in sesame oil (0.1 µg/mL). The test compounds were dissolved in sesame oil and diluted with sesame oil to achieve desired concentrations. The solutions were periodically checked by TLC to insure homogeneity. Injections were made in the nape of the neck for 3 consecutive days. The unstimulated control group received vehicles alone (0.05 mL IPM and 0.1 mL sesame oil each day), while the stimulated control group received 0.1 mL of the estradiol solution (total dose 0.03 µg). All test groups received 0.1 mL of the stimulating dose of estradiol (0.01 µg) plus 0.05 mL of the test compounds solutions each day. The IPM and oil injections were made at separate sites to minimize possible physical or chemical interactions or reduced absorption of either compound. Antiestrogenic activity was measured as a decrease from the estradiol-induced increase in uterine weight seen in the test compound groups versus the estradiol-stimulated group alone. The observed antiestrogenic activities are set out in Table II.

Tamoxifen elicited no antagonistic action at any of the doses tested, while MER 25 and Analog II yielded a dose-dependent decrease in uterine weight. None of the new compounds active in the mouse antiuterotrophic assay showed activity in the immature rat antiuterotrophic assay at doses up to 500 µg (data not shown).

All U.S. patent applications and publications cited herein are hereby incorporated by reference.

Changes may be made in the embodiments of the invention described herein or in parts or elements of the embodiments described herein or in the steps or in the sequence of steps of the methods described herein without departing from the spirit and scope of the invention as defined in the following claims.

What is claimed is:

1. A compound having the formula:

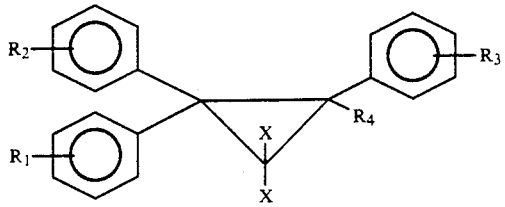

or any pharmaceutically acceptable salt thereof, in which:

$R_1$ is hydrogen, a hydroxyl group, an alkoxy group or a substituted or unsubstituted arylalkoxy group (with the proviso that $R_1$, $R_2$ and $R_3$ are not simultaneously arylalkoxy), and in which any substituent of the aryl group comprises an alkyl group;

$R_2$ is hydrogen, a hydroxyl group (with the proviso that $R_1$ and $R_3$ are not simultaneously alkoxy when $R_2$ is hydroxyl), an alkoxy group or a substituted alkoxy group in which the substituent of the alkoxy group comprises either a dialkylamino group, a heterocycle containing between about 5 and 6 members, at least one of which is nitrogen, or a substituted or unsubstituted aryl group, in which any substituent of the aryl group comprises an alkyl group;

$R_3$ is hydrogen, a hydroxyl group, an alkoxy group or a substituted alkoxy group and in which the substituent of the alkoxy group comprises either a dialkylamino group or a heterocycle containing between about 5 and 6 members, at least one of which is nitrogen, or a substituted or unsubstituted aryl group, in which any substituent of the aryl group comprises an alkyl group;

$R_4$ is hydrogen; and

X is a halogen or hydrogen.

2. The compound of claim 1 in which $R_2$ is an alkoxy group, a beta-dialkylaminoalkoxy group, or an aryloxy group.

3. The compound of claim 2 in which $R_1$ is hydrogen or an alkoxy group.

4. The compound of claim 2 in which $R_3$ is hydrogen or an alkoxy group.

5. The compound of claim 2 in which:
$R_1$ is hydrogen or an alkoxy group; and
$R_3$ is hydrogen or an alkoxy group.

6. The compound of claim 1 in which $R_2$ is a methoxy group, a dimethylaminoethoxy group or an benzyloxy group.

7. The compound of claim 6 in which:
$R_1$ is hydrogen or a methoxy group; and
$R_3$ is hydrogen or a methoxy group.

8. The compound of claim 7 in which X is a halogen.

9. The compound of claim 1 in which $R_1$ is hydrogen, $R_2$ is methoxy, $R_3$ is hydrogen and X is chlorine.

10. The compound of claim 1 in which $R_1$ is hydrogen, $R_2$ is dimethylaminoethoxy, $R_3$ is hydrogen and X is chlorine.

11. The compound of claim 1 in which $R_1$ is methoxy, $R_2$ is dimethylaminoethoxy, $R_3$ is hydrogen and X is chlorine.

12. The compound of claim 1 in which $R_1$ is methoxy, $R_2$ is benzyloxy, $R_3$ is hydrogen and X is chlorine.

13. The compound of claim 1 in which $R_1$ is methoxy, $R_2$ is benzyloxy, $R_3$ is methoxy and X is chlorine.

14. A compound of matter comprising a pharmaceutically acceptable carrier and a compound having the formula:

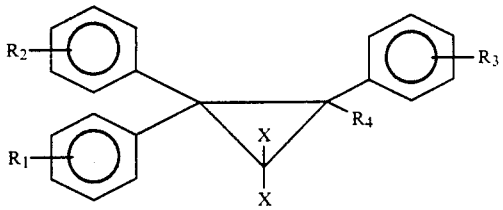

or any pharmaceutically acceptable salt thereof, in which:

- R₁ is hydrogen, a hydroxyl group, alkoxy group or a substituted or unsubstituted arylalkoxy group (with the proviso that R₁, R₂, and R₃ are not simultaneously arylalkoxy), and in which any substituent of the aryl group comprises an alkyl group;
- R₂ is hydrogen, a hydroxyl group (with the proviso that R₁ and R₃ are not simultaneously alkoxy when R₂ is hydroxyl), an alkoxy group or a substituted alkoxy group in which the substituent of the alkoxy group comprises either a dialkylamino group, a heterocycle containing between about 5 and 6 members, at least one of which is nitrogen, or a substituted or unsubstituted aryl group, in which any substituent of the aryl group comprises an alkyl group;
- R₃ is hydrogen, a hydroxyl group, an alkoxy group or a substituted alkoxy group and in which the substituent of the alkoxy group comprises either a dialkylamino group or a heterocycle containing between about 5 and 6 members, at least one of which is nitrogen, or a substituted or unsubstituted aryl group, in which any substituent of the aryl group comprises an alkyl group;
- R₄ is hydrogen; and
- X is a halogen or hydrogen.

15. The compound of claim 14 in which R₂ is an alkoxy group, a beta-dialkyaminoalkoxy group, or an aryloxy group.

16. The compound of claim 15 in which R₁ is hydrogen or an alkoxy group.

17. The compound of claim 15 in which R₃ is hydrogen or an alkoxy group.

18. The compound of claim 15 in which:
- R₁ is hydrogen or an alkoxy group; and
- R₃ is hydrogen or an alkoxy group.

19. A method of inducing antiestrogenic activity in a mammal in need of such therapy comprising administering to the mammal an antiestrogenically effective amount of one or more compounds having the formula:

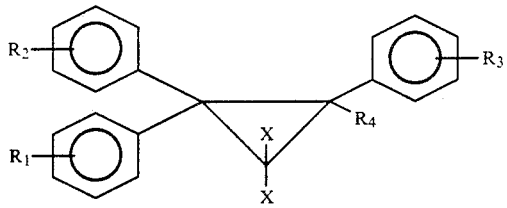

or any pharmaceutically acceptable salt thereof, in which:

- R₁ is hydrogen, a hydroxyl group, an alkoxy group containing from 1 to about 3 carbon atoms, or a substituted or unsubstituted arylalkoxy group (with the proviso that R₁, R₂ and R₃ are not simultaneously arylalkoxy), in which the alkyl group attached to the oxygen atom contains from 1 to about 3 carbon atoms, and in which any substituent of the aryl group comprises an alkyl group containing from 1 to about 3 carbon atoms;
- R₂ is hydrogen, a hydroxyl group (with the proviso that R₁ and R₃ are not simultaneously alkoxy), an alkoxy group containing from 1 to about 3 carbon atoms, or a substituted alkoxy group in which the alkyl group attached to the oxygen atom contains from 1 to about 3 carbon atoms and in which the substituent of the alkoxy group comprises either a dialkylamino group in which each alkyl substituent thereof contains from 1 to about 3 carbon atoms, a heterocycle containing between about 5 and 6 members, at least one of which is nitrogen, or a substituted or unsubstituted aryl group, in which any substituent of the aryl group comprises an alkyl group containing from 1 to about 3 carbon atoms;
- R₃ is hydrogen, a hydroxyl group, an alkoxy group containing from 1 to about 3 carbon atoms, or a substituted alkoxy group in which the alkyl group attached to the oxygen atom contains from 1 to about 3 carbon atoms and in which the substituent of the alkoxy group comprises either a dialkylamino group in which each alkyl substituent thereof contains from 1 to about 3 carbon atoms, or a heterocycle containing between about 5 and 6 members, at least one of which is nitrogen, or a substituted or unsubstituted aryl group, in which any substituent of the aryl group comprises an alkyl group containing from 1 to about 3 carbon atoms;
- R₄ is hydrogen; and
- X is a halogen or hydrogen.

20. The method of claim 19 in which R₂ is an alkoxy group, a beta-dialkyaminoalkoxy group, or an aryloxy group.

21. The method of claim 20 in which R₁ is hydrogen or an alkoxy group.

22. The method of claim 20 in which R₃ is hydrogen or an alkoxy group.

23. The method of claim 20 in which:
- R₁ is hydrogen or an alkoxy group; and
- R₃ is hydrogen or an alkoxy group.

24. A method of inhibiting the development of an estrogen-dependent tumor in a mammal in need of such therapy comprising administering to the mammal an effective amount of one or more compounds having the formula:

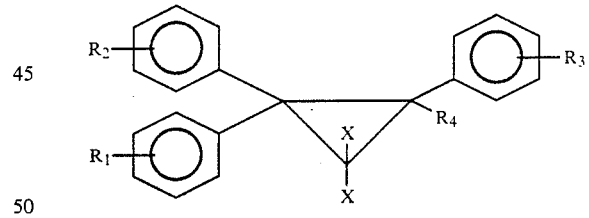

or any pharmaceutically acceptable salt thereof, in which:

- R₁ is hydrogen, a hydroxyl group, an alkoxy group containing from 1 to about 3 carbon atoms, or a substituted or unsubstituted arylalkoxy group (with the proviso that R₁, R₂ and R₃ are not simultaneously arylalkoxy), in which the alkyl group attached to the oxygen atom contains from 1 to about 3 carbon atoms, and in which any substituent of the aryl group comprises an alkyl group containing from 1 to about 3 carbon atoms;
- R₂ is hydrogen, a hydroxyl group (with the proviso that R₁ and R₃ are not simultaneously alkoxy), an alkoxy group containing from 1 to about 3 carbon atoms, or a substituted alkoxy group in which the alkyl group attached to the oxygen atom contains from 1 to about 3 carbon atoms and in which the substituent of the alkoxy group comprises either a dialkylamino group in which each alkyl substituent thereof contains from 1 to about 3 carbon atoms, a heterocycle containing between about 5 and 6 members, at least one of which is nitrogen, or a substituted or unsubstituted aryl group, in which any substituent of the aryl group comprises an alkyl group containing from 1 to about 3 carbon atoms;

$R_3$ is hydrogen, a hydroxyl group, an alkoxy group containing from 1 to about 3 carbon atoms, or a substituted alkoxy group in which the alkyl group attached to the oxygen atom contains from 1 to about 3 carbon atoms and in which the substituent of the alkoxy group comprises either a dialkylamino group in which each alkyl substituent thereof contains from 1 to about 3 carbon atoms, or a heterocycle containing between about 5 and 6 members, at least one of which is nitrogen, or a substituted or unsubstituted aryl group, in which any substituent of the aryl group comprises an alkyl group containing from 1 to about 3 carbon atoms;

$R_4$ is hydrogen; and

X is a halogen or hydrogen.

25. The method of claim 24 in which $R_2$ is an alkoxy group, a beta-dialkyaminoalkoxy group, or an aryloxy group.

26. The method of claim 25 in which $R_1$ is hydrogen or an alkoxy group.

27. The method of claim 25 in which $R_3$ is hydrogen or an alkoxy group.

28. The method of claim 25 in which:

$R_1$ is hydrogen or an alkoxy group; and $R_3$ is hydrogen or an alkoxy group.

* * * * *